(12) United States Patent
McGeoch et al.

(10) Patent No.: US 9,731,125 B2
(45) Date of Patent: Aug. 15, 2017

(54) METHOD AND SYSTEM FOR ALTERING BODY MASS COMPOSITION USING GALVANIC VESTIBULAR STIMULATION

(71) Applicant: THE REGENTS OF THE UNIVERSITY OF CALIFORNIA, Oakland, CA (US)

(72) Inventors: Paul Duncan McGeoch, La Jolla, CA (US); Vilayanur S. Ramachandran, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/770,333

(22) PCT Filed: Feb. 28, 2014

(86) PCT No.: PCT/US2014/019658
§ 371 (c)(1),
(2) Date: Aug. 25, 2015

(87) PCT Pub. No.: WO2014/134564
PCT Pub. Date: Sep. 4, 2014

(65) Prior Publication Data
US 2016/0045733 A1 Feb. 18, 2016

Related U.S. Application Data

(60) Provisional application No. 61/771,766, filed on Mar. 1, 2013.

(51) Int. Cl.
*A61N 1/36* (2006.01)
*A61N 1/05* (2006.01)
(Continued)

(52) U.S. Cl.
CPC ........ *A61N 1/36014* (2013.01); *A61B 5/0531* (2013.01); *A61B 5/0537* (2013.01);
(Continued)

(58) Field of Classification Search
CPC .............. A61N 1/36014; A61N 1/0456; A61N 1/0408; A61N 1/37211; A61N 1/0526;
(Continued)

(56) References Cited

U.S. PATENT DOCUMENTS 6,077,237 A    6/2000   Campbell et al.
6,219,578 B1 *   4/2001   Collins .............. A61N 1/36032
                                                        607/2
(Continued)

FOREIGN PATENT DOCUMENTS

WO       2011161562 A1    12/2011

OTHER PUBLICATIONS

PCT/US2014/109658 International Search Report and Written Opinion, Jun. 6, 2014, 9 pages.
(Continued)

*Primary Examiner* — Rex R Holmes
(74) *Attorney, Agent, or Firm* — Eleanor Musick; Scott Davison; Musick Davison LLP (57) ABSTRACT

A device and method are provided for altering body mass composition in a human subject by applying galvanic vestibular stimulation (GVS) using electrodes placed in electrical contact with the subject's scalp at a location corresponding to each of the subject's left and right vestibular systems. The current source include a feedback loop for measuring a resistance across the subject's scalp and adjusting a voltage output to maintain a constant current across the subject's scalp. GVS may be applied for a predetermined period of time at regular intervals.

14 Claims, 6 Drawing Sheets (51) Int. Cl.
  *A61B 5/053* (2006.01)
  *A61N 1/04* (2006.01)
  *A61N 1/372* (2006.01)
  *A61B 5/00* (2006.01)

(52) U.S. Cl.
  CPC .......... *A61B 5/4836* (2013.01); *A61N 1/0408* (2013.01); *A61N 1/0456* (2013.01); *A61N 1/0526* (2013.01); *A61N 1/37211* (2013.01); *A61B 5/4872* (2013.01); *A61N 1/36032* (2013.01)

(58) Field of Classification Search
  CPC  A61N 1/36032; A61B 5/4836; A61B 5/0537; A61B 5/0531; A61B 5/4872
  See application file for complete search history.

(56) References Cited

U.S. PATENT DOCUMENTS

| | | | |
|---|---|---|---|
| 6,748,275 | B2 | 6/2004 | Lattner et al. |
| 2008/0288016 | A1 | 11/2008 | Amurthur et al. |
| 2009/0082831 | A1 | 3/2009 | Paul et al. |
| 2010/0112533 | A1 | 5/2010 | Chan et al. |
| 2010/0112535 | A1 | 5/2010 | Chan et al. |
| 2010/0113150 | A1 | 5/2010 | Chan et al. |
| 2010/0114187 | A1 | 5/2010 | Chan et al. |
| 2010/0114188 | A1 | 5/2010 | Chan et al. |
| 2010/0114255 | A1 | 5/2010 | Chan et al. |
| 2010/0114256 | A1 | 5/2010 | Chan et al. |
| 2010/0211142 | A1 | 8/2010 | Rogers et al. |
| 2011/0172726 | A1 | 7/2011 | Snyman et al. |
| 2011/0313498 | A1 | 12/2011 | Rogers et al. |
| 2013/0296987 | A1* | 11/2013 | Rogers ............... A61F 7/007 607/112 |

OTHER PUBLICATIONS

Carter, J.R., et al., "Sympathetic responses to vestibular activation in humans", Am J Physiol Regul Integr Comp Physiol; Mar. 2008; 294: R681-R688.

Esposito, A., et al., "Aural Stimulation as Add-on to Diet for Weight Loss: A Preliminary Clinical Study", J Obes Wt Loss Ther vol. 2(9) 1000155, pp. 1-4.

Fitzpatrick, J., et al., "Probing the human vestibular system with galvanic stimulation", J Appl Physiol, Jun. 2004; 96(6): 2301-16.

Fuller, P.M., et al., "Neurovestibular modulation of circadian and homeostatic regulation: Vestibulohypothalamic connection?"; PNAS, Nov. 2002 99(24): 15723-15728.

Gomza, Y.Y., et al., ""The Treatment of Peripheral Vestibular Dysfunction Using Caloric Vestibular Stimulation in Patients with Cerebral Hypertensive Crisis"", Intl J Otolaryn & Head & Neck Surg, May 2015; 4, 229-235.

McGeoch, P.D., et al., "Behavioural evidence for vestibular stimulation as a treatment for central post-stroke pain", J Neurol Neurosurg Psychiatry, 2008; 79:1298-1301.

McGeoch, P.D., et al., "Post-stroke tactile allodynia and its modulation by vestibular stimulation: a MEG case study", Acta Neurol Scand 2009; 119: 404-409.

Ramachandran, V.S., et al., "Rapid relief of thalamic pain syndrome induced by vestibular caloric stimulation", Neurocase, Jun. 2007; 13(3): 185-188.

Ramachandran, V.S., et al., "Can vestibular caloric stimulation be used to treat Dejerine-Roussy Syndrome?", Medical Hypothesis, Dec. 2007, 69(3): 486-488.

EP 14757548.4 Extended European Search Report, mailed Sep. 9, 2016, 11 pages.

Grewal, Trandeep et al, "Frequency-dependent modulation of muscle sympathetic nerve activity by sinusoidal galvanic vestibular stimulation in human subjects", Exp Brain Res (2009) vol. 197 pp. 379-386.

* cited by examiner

Name: XXXXXXXXXXXXXX  Gender: Female  Height: 160.4 cm
Patient ID: XXXXXXXXXX  Ethnicity: Hispanic  Weight: 84.4 kg
DOB: XX-XX-1989  Age: 23

Scan Information:

Scan Date: 10-08-2012
Scan Type: Whole body
Analysis: October 08, 2012 13:53
Version 12.7.3.1
Auto Whole Body
Operator: CK
Model: Discovery W (S/N 82084)
Comment:

DXA Results Summary

| Region | BMC (g) | Fat (g) | Lean (g) | Lean + BMC (g) | Total Mass (g) | % Fat |
|---|---|---|---|---|---|---|
| L Arm | 118.37 | 2120.2 | 2189.7 | 2308.0 | 4428.2 | 47.9 |
| R Arm | 135.21 | 2028.4 | 2773.0 | 2908.2 | 4936.6 | 41.1 |
| Trunk | 462.70 | 19364.9 | 23881.9 | 24344.6 | 43710.4 | 44.3 |
| L Leg | 321.72 | 4481.8 | 7261.1 | 7582.8 | 12064.6 | 37.1 |
| R Leg | 325.62 | 3965.0 | 8388.8 | 8714.4 | 12679.4 | 31.3 |
| Subtotal | 1363.62 | 31961.1 | 44494.5 | 45858.1 | 77819.2 | 41.1 |
| Head | 454.0 | 986.3 | 3487.2 | 3941.2 | 4927.5 | 20.0 |
| Total | 1817.62 | 32947.4 | 47981.7 | 49799.3 | 82746.7 | 39.8 |

FIG. 7

| Name: XXXXXXXXXXXXXX | Gender: Female | Height: 160.4 cm |
| Patient ID: XXXXXXXXXX | Ethnicity: Hispanic | Weight: 84.4 kg |
| DOB: XX-XX-1989 | | Age: 23 |

Scan Information:

| | |
|---|---|
| Scan Date: | 12-07-2012 |
| Scan Type: | Whole body |
| Analysis: | December 07, 2012 09:40 |
| | Version 12.7.3.1 |
| | Auto Whole Body |
| Operator: | CK |
| Model: | Discovery W (S/N 82084) |
| Comment: | |

DXA Results Summary

| Region | BMC (g) | Fat (g) | Lean (g) | Lean + BMC (g) | Total Mass (g) | % Fat |
|---|---|---|---|---|---|---|
| L Arm | 108.9 | 1989.4 | 2440.2 | 2549.1 | 4538.5 | 43.8 |
| R Arm | 136.75 | 1999.0 | 2990.0 | 3127.7 | 5126.7 | 39.0 |
| Trunk | 470.80 | 18941.8 | 25134.3 | 25605.1 | 44546.9 | 42.5 |
| L Leg | 311.24 | 4003.6 | 7632.6 | 7943.9 | 11947.5 | 33.5 |
| R Leg | 342.31 | 3950.1 | 8430.3 | 8772.6 | 12722.8 | 31.0 |
| Subtotal | 1370.00 | 30883.9 | 46628.4 | 47998.4 | 78882.3 | 39.2 |
| Head | 450.22 | 956.0 | 3441.8 | 3892.0 | 4848.0 | 19.7 |
| Total | 1820.22 | 31839.9 | 50070.1 | 51890.4 | 83730.3 | 38.0 |

FIG. 8

METHOD AND SYSTEM FOR ALTERING BODY MASS COMPOSITION USING GALVANIC VESTIBULAR STIMULATION

RELATED APPLICATIONS

This application is a 371 national stage filing of International Application No. PCT/US2014/019658, filed Feb. 28, 2014, which claims the benefit of the priority of U.S. Provisional Application No. 61/771,766, filed Mar. 1, 2013, which is incorporated herein by reference in its entirety.

FIELD OF THE INVENTION

The present invention relates to a device and method for vestibular stimulation to produce physiological changes in an individual's body mass composition.

BACKGROUND OF THE INVENTION

Obesity is a medical condition which involves the accumulation of excess body fat. It is defined by body mass index (BMI), which is a measure of body weight based upon an individual's weight and height. (BMI=mass(kg)/(height(m)) 2). Obesity is defined, by both the World Health Organization and the National Institutes of Health, as a BMI greater than or equal to 30, and pre-obesity is defined as a BMI in the 25 to 30 range. Obesity is one of the leading preventable causes of death worldwide, and is thought to reduce life expectancy by around 7 years. Excess body fat in itself can also cause significant perceived issues with cosmesis in healthy individuals.

Many different techniques have been employed to assist individuals who are overweight to lose weight. These include multiple different types of diet, exercise regimes, weight loss medications and weight loss surgery. There is currently no easy or universally effective weight loss solution.

Osteoporosis is a disease of bones that is characterized by a reduction in bone mineral density (BMD), with the result that there is an increased risk of fracture. The World Health Organization defines osteoporosis as a BMD that is 2.5 standard deviations or more below the mean peak bone mass (average of young, healthy adults) as measured by dual energy X-Ray absorptiometry. The development of osteoporosis is determined by the interplay of three factors: first, an individual's peak BMD; second the rate of bone resorption; third, the rate of formation of new bone during remodelling. It is a particular health concern with aging populations in the developed world, especially in post-menopausal women. A variety of pharmacological treatments have been employed to treat osteoporosis with the mainstay of current management being bisphosphonates, which alter the rate that bone is resorbed.

Centrifugation can in effect mimic a gravitational field greater than that experienced on the surface of the Earth (1G), referred to as "hypergravity" (Smith, 1992). It has been observed that chronic centrifugation of animals leads to an alteration of body mass composition (Fuller et al., 2000; Fuller et al., 2002). In particular, animals subjected to hypergravity via centrifugation exhibit a shift in "the proportional distribution of body mass between fat and fat-free components" (Fuller et al., 2000), with a reduction in body fat that is proportional to field strength (Fuller et al., 2002).

Hypergravity has been reported to specifically bring about a reduction in the body fat of chickens (Evans et al., 1969; Smith & Kelly, 1963; Smith & Kelly, 1965; Burton & Smith, 1996), hamsters (Briney & Wunder, 1962), other domestic fowl (Smith et al., 1975), rabbits (Katovich & Smith, 1978), mice (Oyama & Platt, 1967; Keil, 1969; Fuller et al., 2000; Fuller et al., 2002) and rats (Oyama & Platt, 1967; Oyama & Zeitman, 1967; Pitts et al., 1972; Roy et al., 1996; Warren et al., 1998). The observed decrease in body fat can be quite significant. For example, it has been reported that chickens will decrease from 30% body fat at 1G to 3% at 3G (Burton & Smith, 1996). Similarly, mice living at 2G showed approximately a 55% reduction in absolute and percentage carcass fat (Fuller et al., 2000). This seems to be accompanied by an increased usage of fatty acids as a metabolic substrate, and an increased metabolic rate (Fuller et al., 2006).

While marked loss of fat appears to be the principal change in body mass composition to hypergravity, and with it an increase in the relative size of the body's fat-free component, specific changes to the muscles and bones of animals subjected to chronic centrifugation have also been noted by some authors. Small laboratory animals adapted to a 2G environment have been reported to increase their skeletal mass (as measured using body calcium content) by around 18% (Smith, 1992). Jaekel et al. (1977) also reported that prolonged centrifugation at 2.76G led to an increased bone mineral density in rat thigh bones.

The balance between flexor and extensor muscles has been observed to shift in response to hypergravity to favor muscles with an anti-gravity function (Smith, 1992). In domestic fowl on Earth the leg extensor:flexor muscle mass ratio is 0.85 but 2G altered this ratio to 1.17 (Burton & Smith, 1967; Smith, 1992). There also appears to be a functional difference in the muscles of animals exposed to hypergravity. Animals adapted to 2.5G have been reported to demonstrate a markedly increased exercise capacity (as measured by running to exhaustion), of about three-fold that of non-adapted controls, and an increased maximum oxygen uptake (Burton and Smith, 1967, 1996). Hamsters exposed to a 4G environment for 4 weeks were similarly found to have a greater resistance to fatigue in the gastrocnemius muscle and a 37% increase in the strength of its tetanic contraction (Canonica, 1966).

Functional adaptations in the muscles of rats adapted to hypergravity have been examined by analysis of the protein called myosin heavy chain (MHC) (Fuller et al., 2006). Adult rats exposed to 2G for eight weeks were found to have altered MHC characteristics in their soleus and plantaris muscles (Fuller, 2006). Soleus tends to have more slow-twitch fibers, which are better at endurance activities, and plantaris has relatively more fast-twitch fibers, which are better for sprinting but tend to fatigue more rapidly (Gollnick et al., 1974; Fuller et al., 2006). Fuller et al. (2006) found that the rats adapted to 2G had an increase in the slow twitch form of MHC (MHC1) in their soleus muscles, and a converse increase in the fast twitch form of MHC (MHC2b) in their plantaris muscles.

Several mechanisms have been proposed to explain these physiological changes, either alone or in conjunction, including: alterations in mitochondrial uncoupling proteins; fluid volume shifts; alterations in intracranial pressure; increased loading of skeletal muscles; altered feeding behavior; and activation of the vestibular system (Fuller et al., 2000; Fuller et al., 2002). The vestibular system, which is a major contributor to our sense of balance and spatial orientation, consists in each inner ear of three semicircular canals (which detect rotational movement) and the two otolith organs, termed the utricle and saccule, which detect linear acceleration and gravity (Khan & Chang, 2013). They are called otolith organs as they are fluid filled sacs containing numerous free moving calcium carbonate crystals—called otoliths—which move under the influence of gravity or linear acceleration to act upon receptor cells to alter vestibular afferent nerve activity.

Experiments using mutant mice have suggested that the otolith organs are of particular importance in producing the physiological changes observed in animals subjected to chronic centrifugation. In the first experiment, wildtype mice and a type of mutant mice that lack otolith organs but have intact semicircular canals were subjected to 8 weeks of chronic centrifugation at 2G (Fuller et al., 2002). At the end of this period the percentage body fat was significantly reduced in the wildtype mice living at 2G compared to a control population living at 1G (8.5% cf 15.5%), and the percentage lean muscle mass was significantly increased compared to the control population (91.5% cf 83.1%). However, the mutant mice (lacking otolith organs) living at 2G showed no significant change in their body mass composition compared to mutant mice living at 1G.

The second study involved subjecting wildtype and mutant mice (without otolith organs) to just two hours of centrifugation at 2G (Fuller et al., 2004). In the wildtype mice, the authors reported widespread activation (as determined by c-fos upregulation) of a variety of brain structures known to be important in homeostasis and autonomic nervous system regulation including: the dorsomedial hypothalamus (a brain area thought to be of major importance in overseeing feeding behavior and in fixing a set point for body mass (Fuller et al., 2004)); the parabrachial nucleus; the bed nucleus of the stria terminalis; the amygdala; the dorsal raphe; and the locus ceruleus. These findings were not observed in the mutant mice.

The vestibular nuclei (which are located in the pons and medulla and receive input via the vestibular nerve from the vestibular system) are thought to project (both directly and indirectly via the parieto-insular vestibular cortex (PIVC)) to the brainstem homeostatic sites of the parabrachial nucleus (PB) and the peri-aqueductal gray (PAG) (see Chapter 1 and Chapter 3, Section 8 in doctoral thesis by McGeoch, 2010). The PB seems to act to maintain homeostasis—i.e., a stable internal physiological milieu—by integrating this vestibular input with sympathetic input (via lamina 1 spino- and trigemino-thalamic tract fibers) and parasympathetic input (via the nucleus of the solitary tract) (Balaban and Yates, 2004; Craig, 2007; Craig, 2009; McGeoch et al., 2008, 2009; McGeoch, 2010).

It is thought that the PB then acts to maintain homeostasis by means of behavioral, neuroendocrine, and autonomic nervous system efferent (i.e., both sympathetic and parasympathetic) responses (Balaban and Yates, 2004; McGeoch, 2010). Anatomically the PB projects to the insula and anterior cingulate, amygdala and hypothalamus. The insula and anterior cingulate are areas of cerebral cortex implicated in emotional affect and motivation, and hence behavior (Craig, 2009). The hypothalamus plays a vital role in coordinating the neuroendocrine system and, particularly via its dorsomedial aspect, oversees feeding behavior and fixes a set point for body mass composition (Balaban and Yates, 2004; Fuller et al., 2004; Craig, 2007). The amygdala (together again with the hypothalamus and insula) is similarly known to be important in autonomic nervous system control. The PB also outputs to the PAG and basal forebrain, which are also involved in homeostasis (Balaban and Yates, 2004).

The vestibular system is also known to input to the rostral ventro-lateral medulla (RVLM), which is a major sympathetic control site, and it seems likely that any observed modulatory effect of vestibular stimulation on sympathetic function will, at least in part, be mediated via the RVLM (Bent et al., 2006; Grewal et al., 2009; James & Macefield 2010; James et al., 2010; Hammam et al., 2011). However, as the semicircular canals are not involved in modulating sympathetic outflow during vestibular stimulation (Ray et al., 1998), any sympathetic modulation arising from vestibular stimulation must be attributable to activation of the otolith organs (i.e., the utricle and saccule). It is known that white adipose tissue, which constitutes the vast majority of adipose tissue in the human body, is innervated by the sympathetic nervous system and that this innervation regulates the mass of the adipose tissue and the number of fat cells within it (Bowers et al., 2004).

The sympathetic nervous system is also known to innervate mature long bones and by this means plays a modulatory role in bone remodelling (Denise et al., 2006). Bilateral vestibular lesions in rats lead to a decrease in the mineral density of weight bearing bones (Denise et al., 2006). However, this reduction is prevented by the adrenoceptor antagonist propranolol (Denise et al., 2006), which suggests a direct interaction between the vestibular inputs and the sympathetic nervous system. Hence, it appears that the reported increase in bone mineral density in response to hypergravity (Jaekel et al., 1977; Smith, 1992), may also be mediated by a vestibulo-sympathetic effect.

There are also data showing direct pathways connecting the vestibular nuclei with the dorsomedial hypothalamus (Cavdar et al., 2001), which is the part of the hypothalamus already mentioned as being specifically involved in regulating feeding behavior and setting a fixed point for body mass (Fuller et al., 2004).

The hormone leptin is secreted by fat cells and acts upon the hypothalamus to regulate food intake and energy expenditure. Leptin acts to suppress food intake and increase energy expenditure (Hwa et al., 1997), and as such plays a role in regulating body weight. Notably, vestibular stimulation has been found to cause an increase in leptin release (Sobhani, 2002; Sailesh & Mukkadan, 2014).

A chemical approach to vestibular stimulation may be based on betahistine, a partial histamine-3 (H3) receptor antagonist that has been used for some time to treat Meniere's disease. It is also known that by blocking presynaptic H3 receptors, betahistine causes an increased release of histamine and activation of H1 receptors, which is the opposite action to antihistaminic vestibular suppressants (Barak et al., 2008; Baloh & Kerber, 2011). Some early reports have suggested that, at least in certain subgroups, betahistine may be an effective weight loss medication (Barak et al., 2008). Conversely vestibular suppressant medications often lead to weight gain.

Various techniques have been used for research and clinical purposes to stimulate some or all of the components of the vestibular system in humans (Carter and Ray, 2007). These include: (1) Caloric vestibular stimulation, which involves irrigating the outer canal of the ear with warm or cold water or air and mainly stimulates the lateral semicircular canal of that ear; (2) Yaw head rotations, which activates both lateral semicircular canals; (3) Head-down rotation to activate otolith organs and also, initially, semicircular canals; (4) Linear acceleration, which activates otolith organs; (5) Off-vertical axis rotation (OVAR), which activates otolith organs; (6) Galvanic vestibular stimulation ("GVS"), which activates all five components of the vestibular apparatus simultaneously using an electrical current (Fitzpatrick & Day, 2004; St. George & Fitzpatrick, 2011);

(7) Click induced vestibular stimulation using an auditory click (Watson & Colebatch, 1998); and (8) Neck muscle vibration induced vestibular stimulation (Karnath et al., 2002). Of these techniques, only one offers the practical option of being produced commercially for home use without expert supervision—GVS.

GVS involves stimulating the vestibular system through the transcutaneous application of a small electric current (usually between 0.1 to 3 milliamps (mA)) via two electrodes. The electrodes can be applied to a variety of locations around the head, but typically one is applied to the skin over each mastoid process, i.e., behind each ear. Some authors term this a "binaural application." If a cathode and an anode are used with one placed over each mastoid, which is the most common iteration, then this is termed a bipolar binaural application of GVS. The current can be delivered in a variety of ways, including a constant state, in square waves, a sinusoidal (alternating current) pattern and as a pulse train (Petersen et al., 1994; Carter & Ray, 2007; Fitzpatrick & Day, 2004; St. George & Fitzpatrick, 2011).

An electronic appetite suppressant device known as the FOOD WATCHER™ was available on the market in the United Kingdom until recently. The premise behind the FOOD WATCHER™ was that it would act to electrically activate acupuncture points on the ears, with the consequence that a user's appetite would be suppressed. Additionally it was argued that it may suppress appetite by activating the vagus nerve (Esposito et al., 2012).

The FOOD WATCHER™ electrodes were conically shaped plugs designed to be inserted into the external auditory canals (Esposito et al., 2012). The FOOD WATCHER™ is reported to have generated a "signal with amplitude of 40V, frequency of 50 Hz and current of 40 mA through the ear plugs" (Esposito et al., 2012).

A study was carried out on 40 overweight and obese healthy volunteers to investigate the effectiveness of the FOOD WATCHER™ (Esposito et al., 2012). Ten volunteers received the FOOD WATCHER™ and a hypocaloric diet, ten received a hypocaloric diet alone, ten received the FOOD WATCHER™ and a high-protein diet, and ten a high protein diet alone. The authors found that "after 2 months of simultaneous treatment with electric stimulation and diet there was an average weight loss of 7.07 kg in the hypocaloric group and 9.48 kg in the high-protein group, whereas an average weight loss of 5.9 kg and 7.17 kg were observed with hypocaloric and high-protein diet alone, respectively", leading the authors to conclude that electrical stimulation through the ears may help with weight loss, particularly when used with a high-protein diet, possibly acting via a Yin-yang acupuncture energy balance.

Muscle sympathetic nerve activity (MSNA) to the blood vessels in skeletal muscle can be measured directly in man using microelectrodes. It has been reported that GVS delivered as square wave pulses (at 2 mA of 1 second duration) was ineffective at altering MSNA (Bolton et al., 2004; Carter & Ray, 2007). Conversely, delivering GVS (with an electrode over each mastoid) more dynamically is effective at modulating MSNA. This has been shown using both pulse trains (specifically 10, 1 ms pulses across 30 ms and time-locked to the R wave of the electrocardiogram) (Voustianiouk et al., 2005), and sinusoidal GVS (−2 to 2 mA, 60-100 cycles, applied at administered bipolar binaural GVS (±2 mA, 200 cycles) at frequencies of 0.2, 0.5, 0.8, 1.1, 1.4, 1.7 & 2.0 Hz, to 11 human volunteers while measuring their MSNA (Grewal et al., 2009).

Grewal et al. found a degree of cyclic modulation of MSNA at all frequencies, however, vestibular modulation of MSNA was significantly stronger at 0.2 Hz and significantly weaker at 0.8 Hz. This suggested "that low-frequency changes in vestibular input, such as those associated with postural changes, preferentially modulate MSNA." Conversely, it was proposed that vestibular inputs around the frequency of the heart rate (i.e., 0.8 Hz, which is 48 beats per minute) compete with, and are inhibited by, the modulation of the MSNA by baroreceptors (pressure detecting mechanoreceptors in the walls of blood vessels), which are activated at the frequency of the heart rate.

The baroreceptor reflex is believed to act via the parasympathetic nervous system (including the vagus nerve and nucleus of the solitary tract) to inhibit the action of the RVLM. This inhibition may be mediated, at least in part, via the caudal ventrolateral medulla (Sved et al., 2000).

Additional evidence to support the argument that vestibular inputs with a frequency distinct from the cardiac frequency are more potent at modulating MSNA, is found in a study in which 8 human subjects were given sinusoidal GVS at their own cardiac frequency, and at ±0.1, ±0.2, ±0.3, ±0.6 Hz from this frequency (James & Macefield, 2010). The authors report that the modulatory effect of the GVS on MSNA activity was impaired when its frequency was closer to the cardiac frequency.

The same authors also measured skin sympathetic nerve activity (SSNA), using microelectrodes, in 11 volunteers subjected to bipolar binaural GVS over the mastoid processes (±2 mA, 200 cycles) at 0.2, 0.5, 0.8, 1.1, 1.4, 1.7 and 2.0 Hz (James et al., 2010). Marked entrainment of GVS was found at all frequencies, although it was significantly weaker at 2.0 Hz. In contrast to the pattern observed with vestibular modulation of MSNA (Grewal et al., 2009), it was reported that the pulse related modulation of SSNA was greater at 0.8 Hz than at 0.2 Hz.

In a recent study, this group found that low frequency sinusoidal GVS (at 0.08, 0.13 and 0.18 Hz) caused two peaks of MSNA modulation (Hammam et al., 2011). This suggested that the primary peak occurs from the positive peak of the sinusoid in which the right vestibular nerve is hyperpolarized and the left depolarized, with the secondary peak of MSNA modulation occurring during the reverse scenario. This behavior was not observed at higher frequencies, possibly because there was insufficient time for a secondary peak to be produced. The authors suggest that this finding indicates "convergence of bilateral inputs from vestibular nuclei onto the output nuclei from which MSNA originates, the rostral ventro-lateral medulla."

Various uses for vestibular stimulation have been described in related art, including: treating motion sickness (U.S. Pat. No. 4,558,703 to Mark); headsets for stimulation in a virtual environmental (U.S. Pat. No. 6,077,237 to Campbell, et al.); counteracting postural sway (U.S. Pat. No. 6,219,578 to Collins, et al.); to induce sleep, control respiratory function, open a patient's airway and/or counteract vertigo (U.S. Pat. No. 6,748,275 to Lattner, et al.); an in-ear caloric vestibular stimulation apparatus (U.S. Pat. No. 8,262,717 to Rogers, et al.); and to alleviate anxiety (U.S. Pat. No. 8,041,429 to Kirby).

Patent applications have been filed for the following: a method of delivering caloric vestibular stimulation (US Patent Publication 2011/0313498 to Rogers, et al.) and a system and method for reducing snoring and/or sleep apnea in a sleeping person, which may involve the use of GVS (US Patent Publication 2008/0308112 to Bensoussan). Chan, et al. have filed several patent applications for a variety of uses of GVS including: an adaptive system and method for altering the motion of a person (US Patent Publication 2010/0114256); a system for altering motional responses to sensory input (US Patent Publication 2010/0114255); a system and method for providing therapy by altering the motion of a person (US Patent Publication 2010/0114188); a system and method for providing feedback control in a vestibular stimulation system (US Patent Publication 2010/0114187); a system for altering the motional response to music (US Patent Publication 2010/011418); a system and method for game playing using vestibular stimulation (US Patent Publication 2010/0113150); a system and method of altering the motions of a user to meet an objective (US Patent Publication 2010/0112535); and a system and method of training to perform specified motions by providing motional feedback (US Patent Publication 2010/0112533).

GVS is also known to stimulate all components of the vestibular apparatus, including the two otolith organs, and dynamic forms of GVS (i.e., pulse train and sinusoidal) appear to be effective at modulating sympathetic activity. If bipolar binaural sinusoidal GVS is used, the modulation of MSNA is greater when it is administered at a frequency distinct from the cardiac frequency.

In spite of the many reported uses of GVS in the prior art, there has been no teaching or suggestion to apply GVS to alteration of body mass composition in humans. The present invention is directed to such an application.

SUMMARY OF THE INVENTION

According to the present invention, a system and method are provided for galvanic vestibular stimulation to alter body mass composition in humans. In an exemplary embodiment, sinusoidal or pulse trains of galvanic current are applied via electrodes applied to a subject's scalp to stimulate the otolith organs and activate the vestibular system. The alteration of body mass composition may include one or more of the following effects: a decrease in body fat; a relative increase in lean muscle mass; and an increase in bone mineral density. The present invention may be used to treat obesity, diseases associated with obesity (e.g., type 2 diabetes mellitus and hypertension), osteoporosis, or it may be used as an aid in physical training to improve relative lean muscle mass and improve the exercise capacity of that muscle.

In an exemplary embodiment, vestibular stimulation, preferably via GVS (likely administered in a sinusoidal or pulse-train manner), is applied to modulate body mass composition in order to bring about: a decrease in total body fat; an increase in lean muscle mass; and an increase in bone mineral density. This effect will likely take place via activation of the otolith organs of the inner ear by GVS and subsequent modulation of sympathetic nervous system activity, which is likely to be mediated via the RVLM. Additionally, this effect may also involve brain structures such as brainstem homeostatic sites (specifically the PB, PAG), the PIVC, amygdala, insula and the hypothalamus. The effect may also be mediated via an effect on the release of certain hormones, such as leptin. The efficacy of the invention is likely to be greater if bipolar binaural GVS (with an electrode over each mastoid process) is administered in a dynamic manner (e.g. sinusoidal or pulse train).

In one aspect of the invention, a device for altering body mass composition in a human subject includes electrodes disposed in electrical contact with the subject's scalp at a location corresponding to each of the subject's left and right vestibular system; and a current source in electrical communication with the electrodes for applying galvanic vestibular stimulation (GVS) to the subject. In one embodiment, the current source produces a constant current within a predetermined voltage range. The current source may produce a current having alternating polarity. The current source may further include a feedback loop for measuring a resistance across the subject's scalp and adjusting a voltage output to maintain a constant current across the subject's scalp. The current produced by current source may be within a range of 0.001 mA to 5 mA. The current produced by the current source may be sinusoidal with a frequency that is less than the subject's cardiac frequency.

In another aspect of the invention, a method for altering body mass composition in a human subject comprises applying galvanic vestibular stimulation (GVS) to the subject. The GVS can be applied by disposing an electrode on the subject's scalp proximate to each mastoid process. The GVS may be a current having a constant level and an alternating polarity. In one embodiment, the constant current level can be maintained by a feedback loop adapted to measure a resistance across the subject's scalp and adjust a voltage output to maintain the current level. The GVS may be a sinusoidal current having a frequency that is less than the subject's cardiac frequency. The GVS may be applied for a predetermined period of time at a regular interval, which may be daily, weekly, or a combination thereof.

In yet another aspect of the invention, a method of decreasing total body fat in a human subject in need thereof comprises applying galvanic vestibular stimulation (GVS) to the subject. Still another aspect of the invention is a method of increasing relative percentage lean muscle mass in a human subject in need thereof by applying galvanic vestibular stimulation (GVS) to the subject. In a further aspect of the invention, a method of increasing bone mineral density in a human subject in need thereof includes applying galvanic vestibular stimulation (GVS) to the subject.

BRIEF DESCRIPTION OF THE DRAWINGS

The present invention will be better understood from the following detailed description of some preferred embodiments of the invention, taken in conjunction with the accompanying drawings, in which like numbers correspond to like parts, and in which.

DETAILED DESCRIPTION

Figure 1:
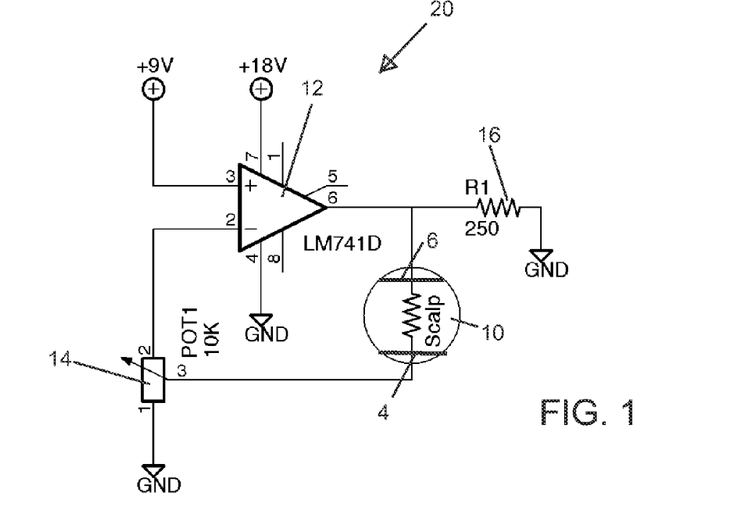
FIG. 1 is a schematic diagram of an exemplary stimulator circuit.
Figure 2:
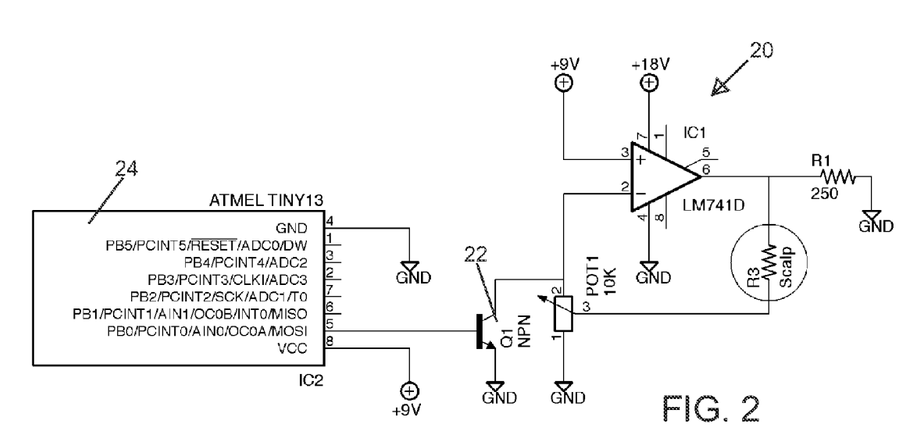
FIG. 2 is a schematic diagram of an alternative embodiment of the stimulator circuit with a gain control component.

FIGS. 1 and 2 illustrate one possible embodiment of the GVS circuitry that can be employed to carry out the method of the present invention. The device 20 includes a source of time-varying galvanic current that may be software programmable using a microcontroller.

FIG. 1 illustrates the basic components of an embodiment of the stimulation device 20, which includes an operational-amplifier ("op-amp") based constant-current source. A voltage is placed across the scalp 10 through electrodes 4 and 6 and measured by the op-amp 12. In the exemplary embodiment, op-amp 12 may be a general purpose operational amplifier, an example of which is the LM741 series op-amp, which is widely commercially available. Selection of an appropriate operational amplifier will be within the level of skill in the art. If the voltage returning from the scalp 10 to pin 2 (inverting input) of op-amp 12 is different than the reference voltage +9V at pin 3 (non-inverting input), the operational amplifier draws from the +18V input through pin 7 to increase the amount of voltage output at pin 6, thereby increasing the current across the scalp 10 to maintain a constant current level. Load resistor 16 is 250 ohms Adjustment of potentiometer 14 provides gain control by decreasing the voltage input into op-amp 12 at pin 2, thus controlling the amount of current flowing across the scalp. In the preferred embodiment, the +9V and +18V inputs are provided by one or more batteries (not shown), or a conventional DC converter may be used with appropriate safety provisions.

The schematic in FIG. 2 adds control components to the basic stimulator circuit 20 of FIG. 1. Transistor 22, powered by the pulse-width-modulation (PWM) output (MOSI (master output/slave input, pin 5) of an ATtiny13 microcontroller 24 (Atmel Corporation, San Jose, Calif.) or similar device, may be used to control the gain of the stimulator. The PWM causes the transistor to draw more or less of the voltage entering the Op-Amp 12 (pin 2) to ground, thus modulating the amount of current flowing across the scalp.

In a preferred embodiment, the device components and any external interfaces will be enclosed within a housing 30 (shown in FIG. 5) with appropriate user controls 32 for selecting stimulation parameters as appropriate. Note that a knob is shown for illustrative purposes only and that other types of controls, including switches, buttons, pressure bumps, slides, touch screens or other interface devices may be used. Optional design components that may be added to expand the functionality of the device include a memory storage device, such as a memory card or electrically erasable programmable read-only memory (EEPROM), which will allow the time, duration, and intensity of stimulations to be recorded. This can be accomplished by programming the microcontroller 24 to output a logic-level 3.4V pulse (TTL (transistor-transistor logic)) from the remaining digital out (MISO (master input/slave output, pin 6) to a secure digital (SD) memory card, EEPROM, USB flash drive or other data storage device via an appropriate port on the device housing. Additionally, the +18V input may be derived by integrating a charge pump, or DC-DC step-up converter, such as the MAX629 or MAX1683 (not shown). This design feature would have the benefit of reducing the size of the device by producing the necessary +18V input from smaller batteries, which can be disposable or lithium ion rechargeable. Additional features may include wireless communication circuitry, as is known in the art, for programming and/or data collection from a remote computing device, which may include a personal computer, smart phone or tablet computer.

Other functions for implementing GVS in the present invention may include the ability to pulse the current at precise intervals and durations, in a sinusoidal wave with adjustable amplitude and period, and even switch polarity at precise intervals.

Additional options for facilitating and/or enhancing the administration of GVS may include a built-in biofeedback capability to adjust the stimulation parameters for optimal effect based on signals generated by sensors that monitor the subject's activity and/or biometric characteristics, such as motion, position, heart rate, etc. For example, real-time heart measured by a heart-rate sensor or monitor can be used as input into the GVS device, triggering an automatic adjustment of the sinusoidal GVS frequency to an appropriate, possibly pre-programmed, fraction of the cardiac frequency. Real-time data on the user's motion or position measured by accelerometers may also be used as input to control stimulation, to improve effectiveness and safety. For example, treatment could be terminated if excessive motion or change in the user's position is detected, or the user can be alerted about changes in position that could have adverse effects. The heart rate sensor/monitor and/or accelerometers may be separate devices that communicate with the inventive GVS device through a wired or wireless connection. Alternatively, sensors may be incorporated directly into the GVS device to form a wearable "sense-and-treat" system. As new sensors are developed and adapted to mobile computing technologies for form "smart", wearable mobile health devices, a "sense-and-treat" GVS device may provide closely tailored stimulation based on a wide array of sensor data input into the device.

Figure 3:
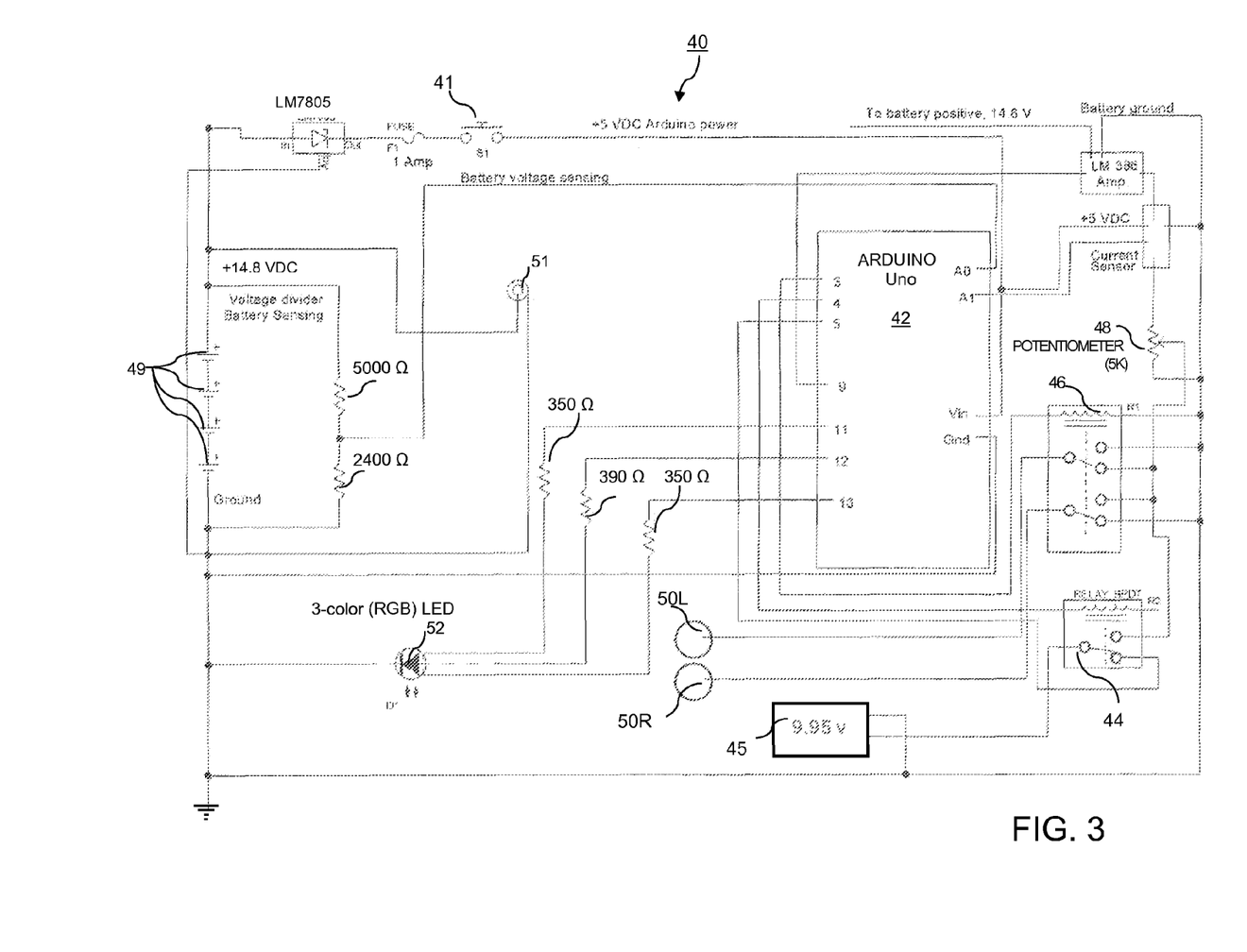
FIG. 3 is a schematic diagram of a second alternative embodiment of the stimulator device.

FIG. 3 schematically illustrates an exemplary prototype of the inventive device 40 implemented using the widely commercially-available ARDUINO® Uno single board microcontroller 42 (Arduino, LLC, Cambridge, Mass.), which is based on the ATmega328 microcontroller (ATMEL® Corporation, San Jose, Calif.). Microcontroller 42 includes fourteen digital input/output pins (of which six can be used as pulse width modulation (PWM) outputs), six analog inputs, a 16 MHz ceramic resonator, a USB connection, a power jack, an ICSP header, and a reset button. The +14.8 V DC power to the circuit is provided by batteries 49. For example, four lithium ion batteries, each providing 3.7V (1300 mAh) are used, and are preferably rechargeable via charging port 51.

Figure 4A:
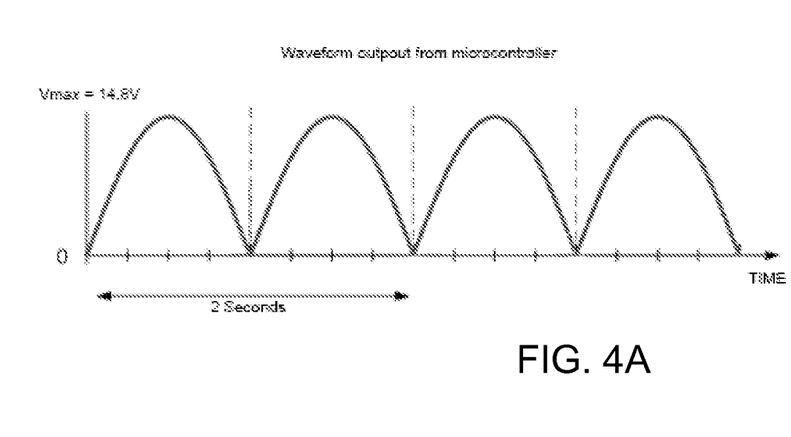
FIGS. 4A and 4B illustrate exemplary wave forms generated by the device.

The PWM allows the output waveform to be accurately controlled. In this case, the waveform takes a repeating half-sine wave pattern in a positive deflection, as shown in FIG. 4A. The frequency has been predefined as 0.5 Hz, but may be set to a different value by manual control or in response to input from a sensor, such as a heart rate sensor (see, e.g., FIG. 5). The user can manually control the amplitude by adjusting the potentiometer 48, allowing a range of 0 to 14.8V to be supplied to the electrodes. This adjustment may be effected by rotating a knob, moving a slide (physically or via a touch screen), or any other known user control mechanism. Alternatively, the potentiometer setting can automatically adjust in response to an input signal from a sensor. Relay 44 communicates the voltage adjustment to a graphical display 45 to provide a read-out of the selected voltage and/or current.

Figure 4B:
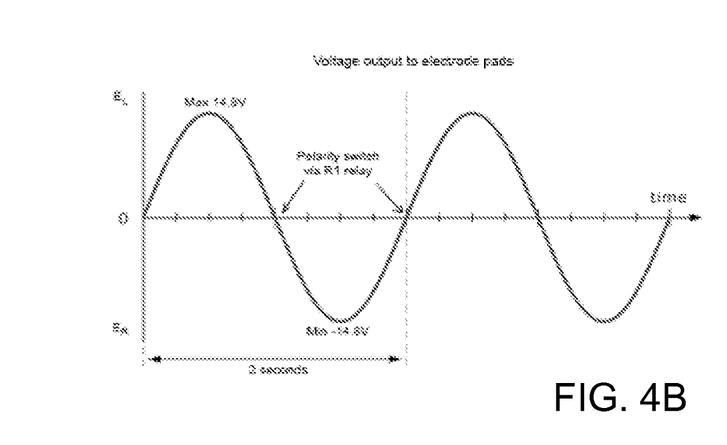

A relay 46 may be employed to effectively reverse the polarity of the current with every second pulse. The effect of this is shown in FIG. 4B, where the sinusoidal pattern changes polarity, thus generating a complete sine waveform to produce alternating periods of stimulation, on the order of 1 second in duration, to the left and right mastoid electrodes 50L and 50R.

The device may optionally include a three color LED 52 that provides a visual display of device conditions, i.e., diagnostic guidance, such as an indication that the device is working correctly or that the battery requires recharging.

Optional design components may include a touch screen configuration that incorporates the potentiometer controls, a digital display of voltage and current, plus other operational parameters and/or usage history. For example, remaining battery charge, previous stimulation statistics and variations in resistance could be displayed. Additional features may include controls for alterations in the waveform such as change of frequency and change of wave type (for example square, pulse or random noise). The ARDUINO® microprocessor platform (or any similar platform) is ideally suited to incorporate feedback control or manual control of frequency, intensity or other stimulation parameters based on an external signal source. For example, the ARDUINO® microprocessor platform, if provided with BLUETOOTH® capability, can be wirelessly controlled by an iPHONE®, ANDROID®, or other smart phone, laptop or personal computer, tablet or mobile device, so that the touchscreen of the mobile device can be used to control and/or display the GVS stimulation parameters rather than requiring a dedicated screen on the device. The mobile device may also be configured to store and analyze data from previous stimulations, providing trends and statistics about long periods of stimulation, such as over 6 months. Applications of this could allow for programs to monitor and guide users on their progress and goals, highlighting body measurements and changes in weight relative to the periods of stimulation.

An exemplary operational sequence for the embodiment of FIG. 3 for use in effecting an alteration in body mass composition may include the following steps:
1. When the push button power switch 41 is activated, the battery(ies) 49 supply 5 volts DC to the microprocessor 42 through a 5 volt regulator and a 1 amp fuse (shown in the figure but not separately labeled.)
2. The LED 52 will flash green three times to indicate the power is "on". If the blue light flashes the battery needs charging. While the voltage is supplied to the electrodes 50L and 50R, the LED 52 will flash red at regular intervals, e.g., 30 seconds to a minute.
3. The microprocessor 42 generates a 0.75 VDC half wave sign wave. The voltage is amplified to 14.8 volts by the amplifier. The sine wave completes one-half cycle in 1 second (i.e., the frequency of the sine wave is 0.5 Hz). The voltage can be varied by the potentiometer 48 from 0 to 14.8 volts.
4. After a half cycle is completed, relay 46 switches polarity of the electrodes 50L, 50R and the microprocessor 42 sends another half cycle. The relay 46 again switches polarity and continues for as long as the unit is "on". This sends a full sine wave of up to ±14.8 VDC to the electrodes, with the full voltage swing modulated by the potentiometer 48.
5. A digital display 45 provides a visual indication of the voltage and current delivered to the electrodes 50L, 50R. Depending on the size and complexity of the display, voltage and current values may be displayed simultaneously or alternately for a short duration, e.g., 3 seconds.

Other device options may include user controls to allow the current to be pulsed at precise intervals and durations, a sinusoidal wave to be generated with adjustable amplitude and period, and/or to switch polarity at precise intervals. External control and monitoring via a smart phone or other mobile device as described above may also be included. Further input and processing capability for interfacing and feedback control through external or internal sensors may be included.

Figure 5:
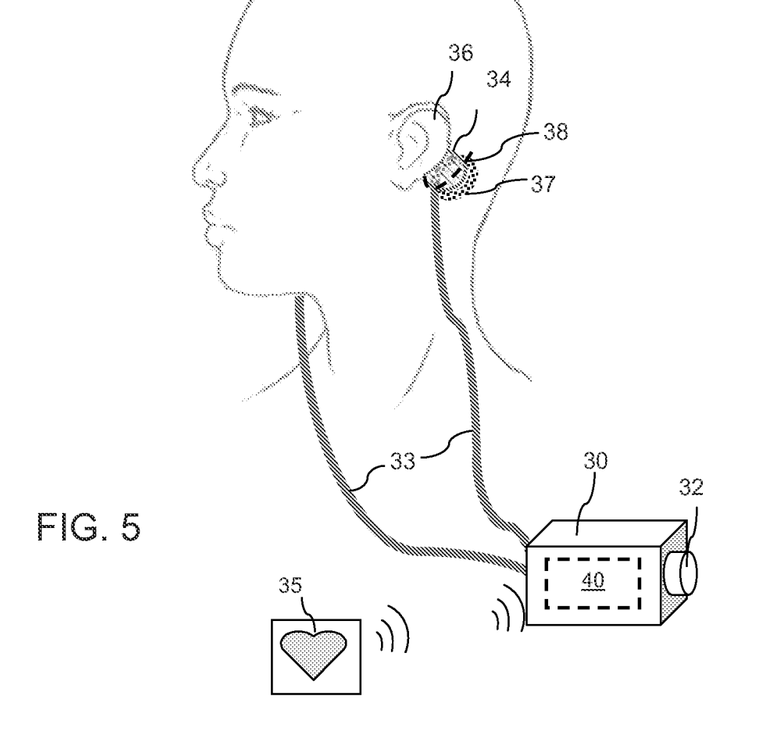
FIG. 5 is a diagram showing an exemplary GVS electrode placement.

FIG. 5 illustrates an exemplary GVS electrode 34 positioned on the skin behind the pinna of the left ear 36, and over the left mastoid process, of a subject to be treated. The mastoid process is represented by dashed line 38. The right electrode (not shown) would be placed in the same manner on the skin over the right mastoid process and behind the right pinna. It should be noted that the illustrated placement of the electrodes is provided as an example only. In fact, laterality of the electrode application, e.g., electrodes precisely over both mastoid processes, is not believed to be critical, as long as each electrode is in sufficient proximity to the vestibular system to apply the desired stimulation. The electrodes 34 are connected to stimulation device 40 (inside housing 30) by leads 33. Manual control means, illustrated here as a simple knob 32, may be operated to control the current or other parameters. As described above, alternative control means include a slide, touch screen, buttons or other conventional control devices. External control signals, for example, a signal from a heart rate monitor 35, may be input into the device either wirelessly, as illustrated, or by leads running between the sensor and the device. Electrodes such as the widely commercially available 2×2 inch platinum electrodes used for transcutaneous electrical nerve stimulation (TENS) may be used in order to minimize any possible skin irritation. A conducting gel 37 may be applied between the subject's scalp and the contact surface of the electrodes to enhance conduction and reduce the risk of skin irritation.

The amount of current the subject actually receives depends on the scalp resistance ($I_{scalp}=V_{electrodes}/R_{scalp}$), which may vary as the user perspires, if the electrode position changes, or if contact with the skin is partially lost. It appears that the current levels quoted in the literature could only be delivered if the scalp resistance was much lower than it actually is. Measurements conducted in conjunction with the development of the inventive method and device indicate that the trans-mastoid resistance is typically between 200 to 500 k-Ohm. Thus, if a GVS device were actually being used to deliver 1 mA, the voltage would be between 200 to 500V according to Ohm's law. The battery-powered devices that are usually used to administer GVS are simply not capable of generating such an output. Hence, the existing reports appear to be inaccurate with regard to the actual current being delivered in GVS.

Prior art designs lack consideration for each subject's unique scalp resistance, and therefore may not deliver an effective current to each patient. In the present invention, this limitation can be overcome by taking into account inter-subject scalp resistance variability as well as compensating for fluctuations in the scalp resistance that may occur throughout the procedure. To compensate for slight and fluctuating changes in scalp resistance during the administration of current, the inventive GVS device may include an internal feedback loop that continuously compares the desired current against the actual measured current across the scalp and automatically compensates for any differences. If $R_{scalp}$ increases, the $V_{electrodes}$ increases to compensate. Conversely, voltage decreases when $R_{scalp}$ drops. This dynamic feedback compensation loop provides constant current across the scalp for the duration of the procedure regardless of fluctuating changes in electrode-scalp impedance.

Figure 6:
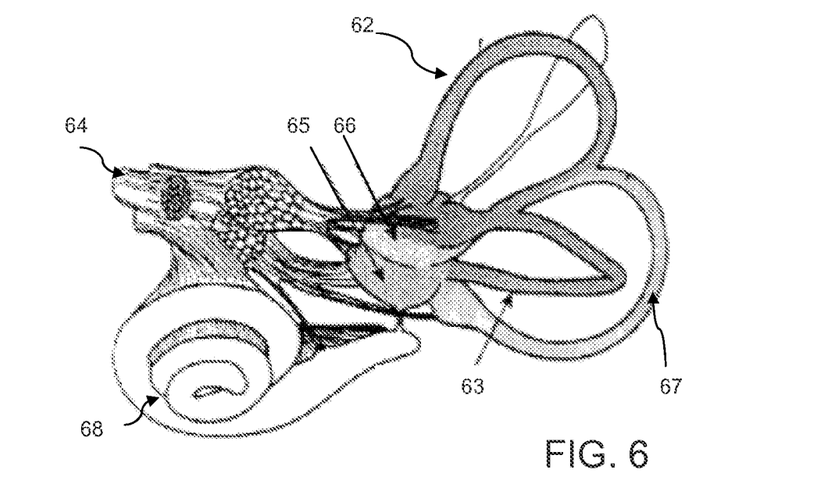
FIG. 6 is a diagram illustrating the vestibular system of the left inner ear.

FIG. 6 illustrates the vestibular system of the left inner ear. The cochlea 68, which is the peripheral organ of hearing, is also shown. It demonstrates: the anterior 62, posterior 67, and horizontal 63 semicircular canals, which transduce rotational movements; and the otolith organs (the utricle 66 and saccule 65), which transduce linear acceleration and gravity. Without intending to be bound by any theory, it is believed that the otolith organs mediate any change in body mass composition that GVS evokes. The vestibulocochlear nerve 64 (also known as the eighth cranial nerve) is composed of the cochlear nerve (which carries signals from the cochlea), and the vestibular nerve (which carries signals from the vestibular system).

Validation

Performance of the present invention was evaluated using dual energy x-ray absorptiometry (DXA), a technique that was originally developed to determine bone mineral density (BMD) and to aid in the management of osteoporosis. More recently, the technique has been expanded to include the analysis of fat mass and lean body mass in addition to BMD. The DXA machine emits alternating high and low energy x-rays that produce precise, high quality images. The use of a fan beam allows decreased scan times so that scans can be completed within seconds or minutes.

The basic principle of DXA data acquisition is based on the differences between bone and soft tissue attenuation at the high and low x-ray levels. As the x-ray beam passes through the subject, detectors register the varying levels of x-rays that are absorbed by the anatomical structures of the subject. The raw scan data, which includes values of tissue and bone, are captured and sent to a computer. An algorithm interprets each pixel, and creates an image and quantitative measurement of the bone and body tissues.

Whole body DXA scans using a HOLOGIC® Discovery W™ DXA scanner were conducted to determine bone mineral density, lean mass and whole body fat. The technique has a precision error (1SD) of 3% for whole body fat and 1.5% for lean mass. The in vivo precision for the measurement of bone density using the DXA technique is 0.5-1.5% at the lumbar spine and the standard deviation of the lumbar spine bone density is 0.01 g/cm$^2$. The radiation risk associated with the proposed protocol used is small and in cumulative total is equal to 0.26 mSv for each subject. This amount of radiation exposure is low, typically less than what one would receive from one year of natural exposure, i.e., around 1.6 mSv.

A comparable commercially available GVS device sold under the trademark VESTIBULATOR™ (Good Vibrations Engineering Ltd. of Ontario, Canada) has previously been used in a number of research studies at other institutions. (Barnett-Cowan & Harris, 2009; Trainor et al., 2009.) This device functions with 8 AA batteries, so that the voltage can never exceed 12 V. According to the manufacturer's specifications, the maximum current that this device can deliver is 2.5 mA. The present invention uses a more user-friendly device (e.g., the delivered current can be adjusted using a controller (knob, slide, or similar) on the side of the housing, in comparison to the VESTIBULATOR™, where a similar adjustment can only be carried out by first writing a MATLAB® script and then uploading it remotely, via BLUETOOTH®, in order to reprogram the VESTIBULATOR's™ settings.)

Due to the very small currents used during GVS, the technique is believed to be safe (Fitzpatrick & Day, 2004; Hanson, 2009). In particular, although electrical current can lead to cardiac arrhythmias, including ventricular fibrillation, the threshold for such an occurrence is in the 75 to 400 mA range, well above the current levels the battery powered GVS devices can deliver. Furthermore, the electrodes will only be applied to the scalp, such as shown in FIG. 5, and nowhere near the skin over the chest.

Resistive heating can occur with high voltage electrical stimulation of the skin. However, the voltage and current (usually below 1 mA) delivered during GVS are well below the levels that pose this risk. Nonetheless, skin irritation can occur due to changes in pH. This may be mitigated by using large surface area (approximately 2 inch diameter) platinum electrodes and aloe vera conducting gels.

It may be desirable to monitor the subject's heart rate (HR) to determine the cardiac frequency during GVS treatment. The cardiac frequency can then be used to alter the frequency of the sinusoidal GVS so as to maintain a certain ratio between the cardiac frequency and the frequency of the sinusoidal GVS to avoid interference with baroreceptor activity. For example, a sinusoidal GVS frequency to cardiac frequency ratio of 0.5 would be appropriate.

During administration of GVS, one platinum electrode is attached to the skin over one mastoid and the other electrode attached to the skin over the other, as shown in FIG. 5. The electrodes may be coated with conducting gel containing aloe vera. The device is activated to deliver a current of approximately 0.1 mA (given a trans-mastoid resistance of about 500 kOhm) with a sinusoidal waveform at 0.5 Hz. A typical current range for the device would be around 0.001 mA to 5 mA. The subject should remain seated or lying flat throughout the session to avoid mishap due to altered balance during vestibular stimulation. The device is set up to automatically stop after one hour however, the subject may discontinue the treatment sooner if desired. The subject should remain seated until their balance has returned to normal, which should occur within a short period of time after the GVS device has been turned off.

Example 1—23 Year Old Female Subject

Data accrued for one human subject support the use of GVS as an effective approach for altering body mass composition to reduce total body fat and increase lean muscle mass. The subject was a Hispanic female born in 1989 and at the time of the study was 23 years old. A cumulative total of 20 hours of GVS was administered between 8 Oct. 2012 and 7 Dec. 2012. Over this two month period, the subject received one hour of GVS on each stimulation day. No GVS session exceeded one hour on any stimulation day.

At the start and completion of the study (after providing a negative pregnancy test), the subject underwent DXA scans as described above. The first DXA scan was carried out on the day of the first GVS session (before the session) and the second scan was carried out five days after the final GVS session. In order to ensure a constant hydration status, the subject was instructed not to exercise within 12 hours of the DXA scans and to refrain from consumption of alcohol, nicotine, and caffeinated beverages. The subject reported that she was at the same stage of her menstrual cycle at the time of each scan. The subject was blinded as to whether she was receiving an experimental or placebo procedure.

The GVS was administered using the bipolar binaural method with an electrode placed on the skin over each mastoid process (see FIG. 5). A linear stimulus isolator from World Precision Instruments (A395D) was used to administer the stimulus, and a 0.5 Hz sinusoidal waveform was imposed on this stimulus by a signal generator from BK Precision (Model 4010A). The subject was seated with her eyes open throughout the administration. The subject's approximate trans-mastoid resistance (after preparing the skin with micro-abrasive gel) was approximately 500 kOhm. To achieve the desired level of stimulation, the current delivered throughout each of the GVS sessions was approximately 0.1 mA. The subject reported being aware of a swaying sensation during each stimulation session. The subject made no changes to her dietary habits and did not engage in exercise during the study period. She was on no regular medications.

Figure 7:
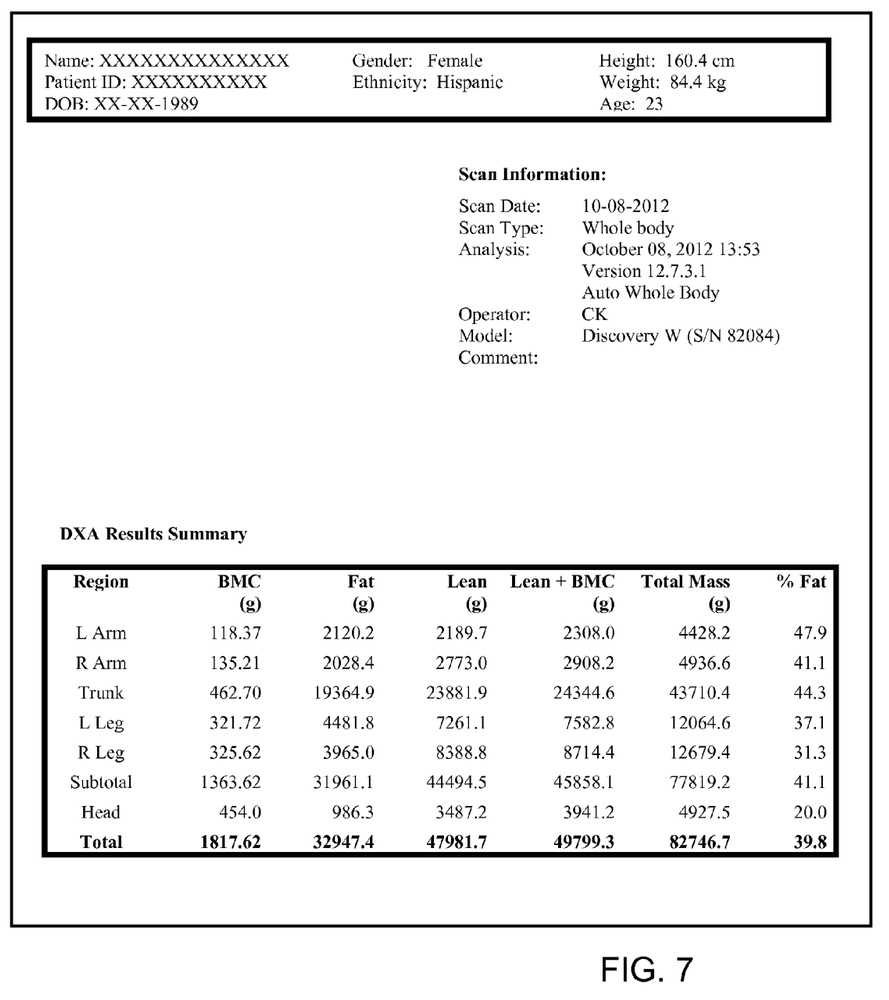
FIG. 7 is a sample report showing the results of a first DXA scan of a human subject.
Figure 8:
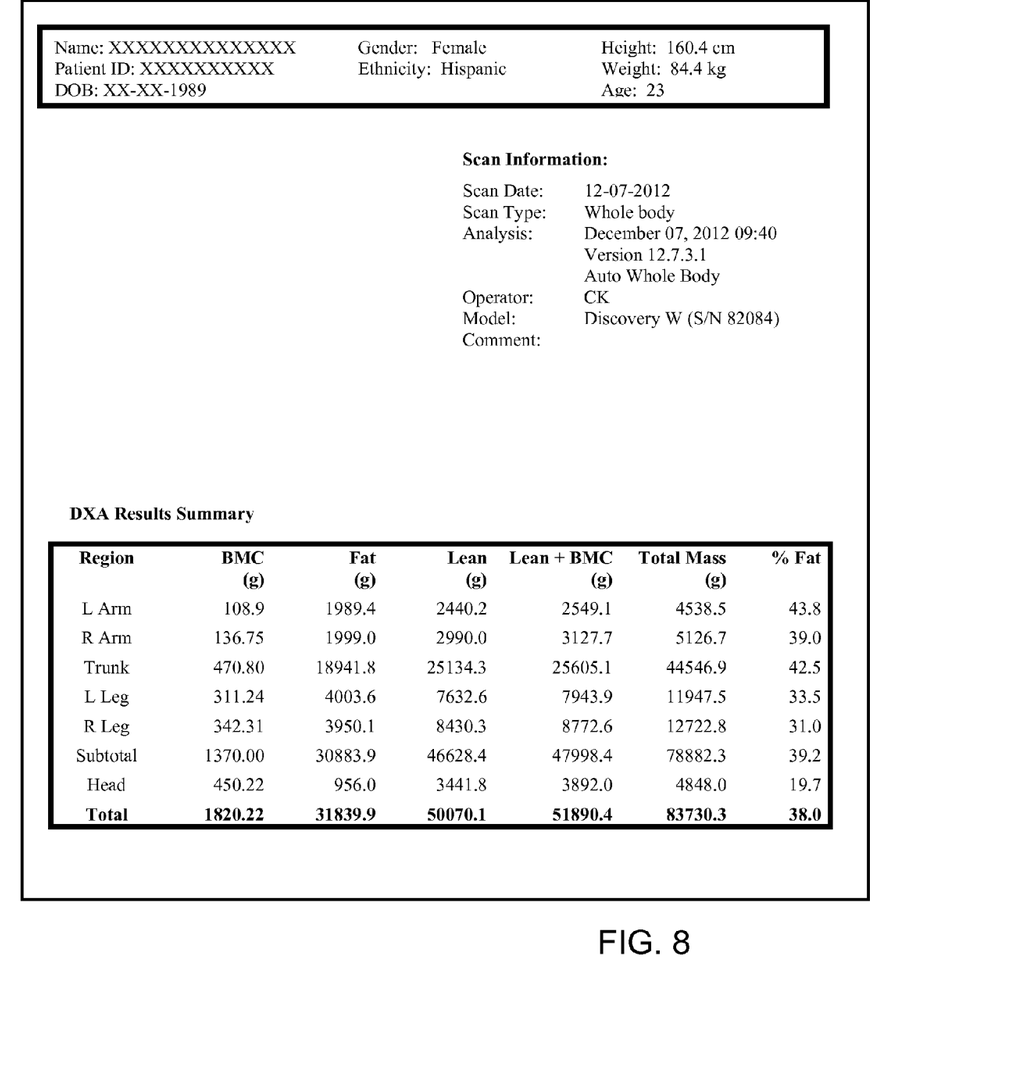
FIG. 8 is a sample report showing the results of a second DXA scan of the same human subject following a series of GVS stimulations.

The report for the initial baseline DXA scan is provided in FIG. 7. Prior to treatment, testing indicated that the subject had a total body fat of 32947.4 g; a total combined bone mineral content (BMC) and lean muscle mass of 49799.3 g; and a percentage body fat of 39.8%. The second DXA scan performed after conclusion of the treatment period produced the results shown in FIG. 8. The post-treatment results indicated total body fat of 31839.9 g; a total combined BMC and lean muscle mass of 51890.4 g; and a percentage body fat of 38.0%. (The BMC is directly proportional to the BMD, which as described above is used in the diagnosis of osteoporosis).

Between the two scans, the subject's combined BMC and lean muscle mass increased by 2091.1 g and total body fat decreased by 1107.5 g. Compared to the baseline scan, this represents an increase in combined BMC and lean muscle mass of 4.2% and a decrease in total body fat of 3.4%. The subject's ratio of total fat to combined BMC and total lean muscle mass improved from 0.66 to 0.61. The data from this subject are thus supportive of the method of using GVS to alter body mass composition as described.

The inventive system and method are based on a novel use of vestibular stimulation, in particular, galvanic vestibular stimulation, to produce physiological changes in an individual human's body mass composition. The application of GVS as described herein simulates some of the effects of hypergravity, providing a safe, simple, drug-free approach to reduce body fat, increase lean muscle mass and increase bone density. The simplicity of the device and its operation makes it possible for any individual wishing to modify his or her body mass composition, regardless of whether for health, aesthetic, or athletic performance reasons, to administer stimulation in the privacy of their home. The device may also be used in a medical facility such as a doctor's office, clinic, or physical therapy facility to treat obesity and associated diseases, treat or prevent osteoporosis, and assist in physical training or recovery from injury.

REFERENCES

Balaban C D, Yates B J. 2004. Vestibulo-autonomic interactions: a teleologic perspective. In: Highstein S M, R. Fay R R, Popper A N, editors. Springer handbook of auditory research: the vestibular system. New York: Springer-Verlag. p. 286-342.

Baloh R W, Kerber K A. Clinical neurophysiology of the vestibular system. Oxford University Press, Oxford, 2011.

Barak N, Greenway F L, Fujioka K, Aronne U, Kushner R F. Effect of histaminergic manipulation on weight in obese adults: a randomized placebo controlled trial. Int J Obes (Lond) 2008; 32: 1559-1565.

Barnett-Cowan M, Harris L R. Perceived timing of vestibular stimulation relative to touch, light and sound. Exp Brain Res 2009; 198: 221-231.

Bent L R, Bolton P S, Macefield V G. Modulation of muscle sympathetic bursts by sinusoidal galvanic vestibular stimulation in human subjects. Exp Brain Res 2006; 174: 701-711.

Bolton P S, Wardman D L, Macefield V G. Absence of short-term vestibular modulation of muscle sympathetic outflow, assessed by brief galvanic vestibular stimulation in awake human subjects. Exp Brain Res 2004; 154: 39-43.

Bowers R R, Festuccia W T, Song C K, Shi H, Migliorini R H, Bartness T J. Sympathetic innervation of white adipose tissue and its regulation of fat cell number. Am J Physiol Regul Integr Comp Physiol 2004; 286: R1167-R1175.

Briney S R, Wunder C C. Growth of hamsters during continual centrifugation. Am J Physiol 1962; 203: 461-464.

Burton R R, Smith A H. Muscle size, gravity and work capacity. Proceedings of the XVI International Congress of Aviation and Space Medicine, Lisbon, Portugal 1967.

Burton R R, Smith A H. Adaptation to acceleration environments. In: Handbook of Physiology. Environmental Physiology. Bethesda, Md., Am Physiol Soc 1996, sect. 4, vol II, chapt. 40, p. 943-974.

Canonica P G. Effects of prolonged hypergravity stress on the myogenic properties of the gastrocnemius muscle. Masters dissertation, University of South Carolina 1966.

Craig A D. Mechanisms of thalamic pain. In: Henry J L, Panju A, Yashpal K, editors. Central neuropathic pain: focus on poststroke pain. Seattle: IASP Press. 2007 p. 81-99.

Craig A D. How do you feel—now? The anterior insula and human awareness. Nat Rev Neurosci 2009; 10: 59-70.

Carter J C, Ray C A. Sympathetic response to vestibular activation in humans. Am J Physiol Regul Integr Comp Physiol 2008; 294: R681-8.

Cavdar S, San T, Aker R, Sehirli U, Onat F. Cerebellar connections to the dorsomedial and posterior nuclei of the hypothalamus in the rat. J Anat 2001; 198: 37-45.

Denise P, Normand H, Wood S. 2006. Interactions among the vestibular, autonomic and skeletal systems in artificial gravity. In: Clement G, Bukley A, editors. Artificial gravity. New York: Springer. p. 233-47.

Esposito A, Fistetto G, Di Cerbo A, Palmieri B. Aural stimulation as add-on to diet for weight loss: a preliminary clinical study. J Obes Wt Loss Ther 2012; 2.

Evans J W, Smith A H, Boda J M. Fat metabolism and chronic acceleration. Am J Physiol 1969; 216: 1468-1471.

Fitzpatrick R C, Day B L. Probing the human vestibular system with galvanic stimulation. J Appl Physiol 2004; 96: 2301-16.

Fuller P M, Warden C H, Barry S J, Fuller C A. Effects of 2-G exposure on temperature regulation, circadian rhythms, and adiposity in UCP2/3 transgenic mice. J Appl Physiol 2000; 89: 1491-1498.

Fuller P M, Jones T A, Jones S M, Fuller C A. Neurovestibular modulation of circadian and homeostatic regulation: Vestibulohypothalamic connection? Proc Natl Acad Sci USA 2002; 99: 15723-15728.

Fuller P M, Jones T A, Jones S M, Fuller C A. Evidence for macular gravity receptor modulation of hypothalamic, limbic and autonomic nuclei. Neuroscience 2004; 129: 461-471.

Fuller P M, Baldwin K M, Fuller C A. Parallel and divergent adaptations of rat soleus and plantaris to chronic exercise and hypergravity. Am J Physiol Regul Integr Comp Physiol 2006; 290: R442-R448.

Gollnick P D, Sjoedin B, Karlsson J, Jansson E, Saltin B. Human soleus muscle: A comparison of fiber composition and enzyme activities with other leg muscles. Pfluegers Archiv 1974; 348: 247-255.

Grewal T, James C, Macefield V G. Frequency-dependent modulation of muscle sympathetic nerve activity by sinusoidal galvanic vestibular stimulation in human subjects. Exp Brain Res 2009; 197: 379-386.

Hammam E, James C, Dawood T, Macefield V G. Low-frequency sinusoidal galvanic stimulation of the left and right vestibular nerves reveals two peaks of modulation in muscle sympathetic nerve activity. Exp Brain Res 2011; 213: 507-514.

Hanson J. Galvanic vestibular stimulation: applied to flight training. 2009. Masters of Science in Electrical Engineering Thesis. California Polytechnic State University.

Hwa J J, Fawzi A B, Graziano M P, Ghibaudi L, Williams P, Van Heek M, Davis H, Rudinski M, Sybertz E, Strader C D. Leptin increases energy expenditure and selectively promotes fat metabolism in ob/ob mice. Am J Physiol 1997; 272: R1204-1209.

Jaekel E, Amtmann E, Oyama J. Effect of chronic centrifugation on bone density in the rat. Anat Embryol 1977; 151: 223-232.

James C, Macefield V G. Competitive interactions between vestibular and cardiac rhythms in the modulation of muscle sympathetic nerve activity. Auton Neurosci 2010; 158: 127-131.

James C, Stathis A, Macefield V G. Vestibular and pulse-related modulation of skin sympathetic nerve activity during sinusoidal galvanic vestibular stimulation in human subjects. Exp Brain Res 2010; 202: 291-298.

Karnath H O, Reich E, Rorden C, Fetter M, Driver J. The perception of body orientation after neck-proprioceptive stimulation: Effects of time and of visual cuing. Exp Brain Res 2002; 143: 350-358.

Katovich M, Smith A. Body mass, composition, and food intake in rabbits during altered acceleration fields. J Appl Physiol 1978; 45: 51-55.

Keil L C. Changes in growth and body composition of mice exposed to chronic centrifugation. Growth 1969; 33: 83-88.

Khan S, Chang R. Anatomy of the vestibular system: a review. NeuroRehabilitation 2013; 32: 437-443.

McGeoch P D. The modulation of central pain by vestibular stimulation and another study on human brain function. Doctoral thesis, University of Aberdeen, 2010.

McGeoch P D, Williams L E, Lee R R, Ramachandran V S. Behavioural evidence for vestibular stimulation as a treatment for central post-stroke pain. J Neurol Neurosurg Psychiatry 2008; 79:1 298-1301.

McGeoch P D, Williams L E, Song T, Lee R R, Huang M, Ramachandran V S. Post-stroke tactile allodynia and its modulation by vestibular stimulation: a MEG case study. Acta Neurol Scand 2009; 119: 404-409.

Oyama J and Platt W T. Reproduction and growth of mice and rats under conditions of simulated increased gravity. Am J Physiol 1967; 212: 164-166.

Oyama J, Zeitman B. Tissue composition of rats exposed to chronic centrifugation. Am J Physiol 1967; 213: 1305-1310.

Petersen H, Magnusson M, Fransson P A, Johansson R. Vestibular disturbance at frequencies above 1 Hz affects human postural control. Acta Otolaryngol 1994; 114: 225-230.

Pitts G C, Bull L S, Oyama J. Effect of chronic centrifugation on body composition of the rat. Am J Physiol 1972; 223: 1944-1948.

Ray C A, Hume K M, Steele S L. Sympathetic nerve activity during natural stimulation of horizontal semicircular canals in humans. Am J Physiol Regul Integr Comp Physiol 1998; 275: R1274-R1278.

Roy R R, Roy M E, Talmadge R J, Mendoza R, Grindeland R E, Vasques M. Size and myosin heavy chain profiles of rat hindlimb extensor muscle fibers after 2 weeks at 2G. Aviat Space Environ Med 1996; 67 (9): 854-858.

Sailesh K S, Mukkadan J K. Vestibular modulation of endocrine secretions—a review. Int J Res Health Sci 2014; 2(1): 0-0

St George R J, Fitzpatrick R C. The sense of self-motion, orientation and balance explored by vestibular stimulation. J Physiol 2011; 589: 807-813.

Smith A H. Centrifuges: their development and use in gravitational biology. ASGSB Bulletin 1992; 5(2): 33-41.

Smith A H, Kelly C F. Influence of chronic acceleration upon growth and body composition. Ann NY Acad Sci 1963; 110: 410-424.

Smith A H, Kelly C F. Biological effects of chronic acceleration Naval Res Rev 1965; 18: 1-10.

Smith A H, Sanchez O, Burton R R. Gravitational effects on body composition in birds. Life Sci Space Res 1975; 13: 21-27.

Sobhani I, Buyse M, Goiot H, Weber N, Laigneau J P, Henin D, Soul J C, Bado A. Vagal stimulation rapidly increases leptin secretion in human stomach. Gastroenterology 2002; 122: 259-263.

Sved A F, Ito S, Madden C J. Baroreflex dependent and independent roles of the caudal ventrolaterl medulla in cardiovascular regulation. Brain Res Bull 2000; 51: 129-133.

Trainor U, Gao X, Lei J J, Lehtovaara K, Harris L R. The primal role of the vestibular system in determining musical rhythm. Cortex 2009; 45: 35-43.

Voustianiouk A, Kaufmann H, Diedrich A, Raphan T, Biaggioni I, MacDougall H, Ogorodnikov D, Cohen B. Electrical activation of the human vestibule-sympathetic reflex. Exp Brain Res 2005; 171: 251-261.

Warren L E, Horwitz B A, Fuller C A. Effects of 2G on lean and obese Zucker rats (Abstract). Fourteenth Annual Meeting Am Soc Gravitational and Space Biol. 1998.

Watson S R D, Colebatch J G. Vestibular-evoked electromyographic responses in soleus: a comparison between click and galvanic stimulation. Exp Brain Res 1998; 119: 504-510.

The invention claimed is:

1. A device for altering body mass composition in a human subject, the device comprising:
   electrodes disposed in electrical contact with the subject's scalp at a location corresponding to each of the subject's left and right vestibular systems; and
   a current source in electrical communication with the electrodes for applying galvanic vestibular stimulation (GVS) to the subject, wherein the current source further comprises a feedback loop for measuring a resistance across the subject's scalp and adjusting a voltage output to maintain a constant current across the subject's scalp, and wherein the current source produces a current within a range of 0.001 mA to 5 mA.

2. The device of claim 1, wherein the current source includes a controller, and further comprises:
   an external sensor for detecting a condition of the subject and generating a signal corresponding to the detected condition;
   a communication device for inputting the sensor signal to the device;
   wherein the controller adjusts a characteristic of the GVS in response to the detected condition.

3. The device of claim 2, wherein the external sensor is a heart rate monitor and the characteristic of the GVS that is adjusted in response to the sensor signal is frequency.

4. A method for altering body mass composition in a human subject, the method comprising:

applying galvanic vestibular stimulation (GVS) to the subject, wherein altering body mass composition comprises one or more of decreasing total body fat, increasing relative percentage lean muscle mass, and increasing bone mineral density in the human subject, and wherein the GVS comprises a current having a constant level and an alternating polarity.

5. The method of claim 4, wherein the GVS is applied by disposing an electrode on the subject's scalp proximate to each mastoid process.

6. The method of claim 4, wherein the constant current level is maintained by a feedback loop adapted to measure a resistance across the subject's scalp and adjust a voltage output to maintain the current level.

7. The method of claim 4, wherein the GVS comprises a sinusoidal current having a frequency that is less than the subject's cardiac frequency.

8. The method of claim 4, wherein the GVS is adjusted in response to input from an external sensor.

9. The method of claim 8, wherein the external sensor is a heart rate monitor.

10. The method of claim 4, wherein altering body mass composition by decreasing total body fat is utilized as a treatment for diabetes.

11. The method of claim 4, wherein altering body mass composition by decreasing total body fat is utilized as a treatment for obesity.

12. The method of claim 4, wherein altering body mass composition by increasing bone mineral density is utilized as a treatment for osteoporosis.

13. A method for altering body mass composition in a human subject, the method comprising:
applying galvanic vestibular stimulation (GVS) to the subject, wherein altering body mass composition comprises one or more of decreasing total body fat, increasing relative percentage lean muscle mass, and increasing bone mineral density in the human subject, wherein the GVS comprises a square wave current.

14. A device for altering body mass composition in a human subject, the device comprising:
electrodes disposed in electrical contact with the subject's scalp at a location corresponding to each of the subject's left and right vestibular systems; and
a current source in electrical communication with the electrodes for applying galvanic vestibular stimulation (GVS) to the subject, wherein the current source further comprises a feedback loop for measuring a resistance across the subject's scalp and adjusting a voltage output to maintain a constant current across the subject's scalp, wherein the current source is configured for producing a square wave current.

* * * * *